(12) United States Patent
Omar

(10) Patent No.: US 6,200,571 B1
(45) Date of Patent: * Mar. 13, 2001

(54) METHODS AND COMPOSITIONS FOR THE TREATMENT OF SEXUAL DYSFUNCTION IN HUMANS AND ANIMALS

(76) Inventor: Lotfi Ismail Omar, P.O. Box F396, Kew Gardens, NY (US) 11415

( * ) Notice: Subject to any disclaimer, the term of this patent is extended or adjusted under 35 U.S.C. 154(b) by 0 days.

This patent is subject to a terminal disclaimer.

(21) Appl. No.: 09/330,423

(22) Filed: May 28, 1999

Related U.S. Application Data

(63) Continuation-in-part of application No. 09/023,652, filed on Feb. 7, 1998, which is a continuation-in-part of application No. 08/660,875, filed on Jun. 10, 1996, now Pat. No. 5,730,987.

(51) Int. Cl.[7] .................................................... A61K 35/78
(52) U.S. Cl. ...................... 424/195.1; 561/451; 561/641; 561/682; 561/702; 514/78
(58) Field of Search ................................. 424/195.1, 561, 424/451, 641, 682, 702; 514/78

(56) References Cited

PUBLICATIONS

The Merck Manual of Diagnosis and Therapy, Merck & Co., Rahway, NJ, 1992.*
Choudhary et al., Chemistry in Britain 33(10): 25–27 (1997).*

* cited by examiner

*Primary Examiner*—Jean C. Witz

(57) ABSTRACT

Therapeutic composition for the treatment of sexual dysfunction and infertility in humans and animals and methods for the treatment of sexual dysfunction and infertility and the improvement of sexual desire in humans and animals by the administration of the composition. The composition comprises fish roe. The methods comprise the administration of fish roe and the administration of fish roe with yohimbine, estrogens, clomiphene, and *Ginkgo biloba*.

6 Claims, No Drawings

METHODS AND COMPOSITIONS FOR THE TREATMENT OF SEXUAL DYSFUNCTION IN HUMANS AND ANIMALS

CROSS-REFERENCE TO RELATED APPLICATIONS

This application is a continuation-in-part of my application Ser. No. 09/023,652, filed Feb. 7 1998, entitled "Composition for treating impotence in men containing dried roe and yohimbine," currently pending, which is a continuation-in-part of my application Ser. No. 08/660,875, filed Jun. 10, 1996, entitled "Medication for Impotence Containing Lyophilized Roe and a Powdered Extract of *Ginkgo biloba*," now U.S. Pat. No. 5,730,987, both of which are incorporated herein by reference in their entirety.

FIELD OF THE INVENTION

The present invention relates generally to a therapeutic composition for the treatment of sexual dysfunction and infertility in humans and animals and, in particular to a composition capable of improving sexual desire in humans and animals, improving erection in male humans and animals, and improving vaginal lubrication, sensitivity, and engorgement in female humans and animals by using fish roe either alone or in combination with *Ginkgo biloba*, yohimbine, estrogens, or clomiphene.

BACKGROUND OF THE INVENTION

Sexual dysfunction in humans and animals involves a multitude of physiological and/or psychological factors. Sexual dysfunction in male humans and animals involves lack of penile erection and sexual desire. Sexual dysfunction in female humans and animals involves lack of sexual desire and lack of vaginal lubrication, sensitivity, and engorgement. To engage in satisfying sexual intercourse both partners must be stimulated both psychologically and physically, their sex organs must function and they must have sufficient sexual desire.

In male humans and animals sufficient sexual desire and penile erection are necessary for proper sexual function. There are a variety of pharmacological and surgical options for those suffering from erectile dysfunction however, each option is not without its risks. Available pharmacological options for human males include sildenafil and alprostadil while surgical options include flexible and inflatable penile implants. However, there is a lack of treatment options proven to increase the level of sexual desire.

For male animals, particularly race horses and endangered species, there is a great need for a pharmacologic option to improve breeding. Current optuion include yohimbine and hormone therapy, both of which offer only limited success.

In female humans and animals sufficient sexual desire and sufficient vaginal lubrication, sensitivity, and engorgement are necessary for proper sexual function. For female humans, various options are available for vaginal dryness that include hormone replacement therapy and vaginal lubricants among others. Unfortunately there are many adverse reactions associated with the pharmacological treatments and the vaginal lubricants do not treat the underlying cause of vaginal dryness. In addition none of these choices offers a risk free choice which also increases the level of sexual desire. Infertility in humans and animals is treated pharmacologically or surgically and each choice is associated with significant risk.

SUMMARY OF THE INVENTION

It is, therefore, a primary object of the present invention to provide a therapeutic composition to treat sexual dysfunction and improve sexual desire in humans and animals.

It is a further object of the present invention to provide a therapeutic composition to treat infertility in humans and animals.

It is yet a further object of the present invention to provide a therapeutic composition to treat erectile dysfunction and improve penile erection in male humans and animals.

It is another object of the present invention to provide a therapeutic composition to increase vaginal lubrication, sensitivity, and engorgement in female humans and animals.

It is also an object of the present invention to provide a therapeutic composition to treat sexual dysfunction in female humans and animals.

It is a further object of the present invention to provide a therapeutic composition to increase sexual desire in humans and animals.

It is yet a further object of the present invention to provide a therapeutic composition to treat sexual dysfunction and infertility that is safe, effective, and easy to administer with minimal or no side effects.

An additional object of the present invention is to instill confidence in humans of their sexual ability.

It is still a further object of the present invention to provide a therapeutic composition to treat sexual dysfunction and infertility in humans and animals that consists of fish roe alone and in a formulation with *Ginkgo biloba* or clomiphene.

It is another object of the present invention to provide a therapeutic composition to improve penile erection, and sexual desire in male humans and animals that includes fish roe in a formulation with a member selected from the group consisting of *Ginkgo biloba*, *Ginkgo biloba* leaf extract, yohimbine, and yohimbine hydrochloride.

It is also an object of the present invention to provide a therapeutic composition to improve vaginal lubrication, sensitivity, and engorgement in female humans and animals that includes fish roe in a formulation with a member selected from the group consisting of *Ginkgo biloba*, *Ginkgo biloba* leaf extract, and estrogens.

It is a further object of the present invention to provide a product that will dramatically improve the sexual activity of humans and animals.

It is yet a further object of the present invention to provide a therapeutic composition that will dramatically improve the fertility of humans and animals.

It is a final object of the present invention to provide a therapeutic composition to treat sexual dysfunction and infertility in humans and animals that is economical in cost to the manufacturer and the consumer.

In accordance with the teachings of the present invention, disclosed herein is a therapeutic composition capable of treating sexual dysfunction and infertility in humans and animals. The therapeutic composition to treat sexual dysfunction in male humans and animals comprises fish roe and a member selected from the group consisting of *Ginkgo biloba*, *Ginkgo biloba* leaf extract yohimbine, and yohimbine hydrochloride. The therapeutic composition to treat sexual dysfunction in female humans and animals comprises fish roe and a member selected from the group consisting of *Ginkgo biloba*, *Ginkgo biloba* leaf extract, and estrogens. The therapeutic composition to treat infertility in humans and animals is comprised of fish roe and a member selected from the group consisting of *Ginkgo biloba*, *Ginkgo biloba* leaf extract, clomiphene, and clomiphene citrate.

In accordance with the teachings of the present invention, disclosed herein is a method for the treatment of sexual dysfunction and infertility in humans and animals. This method includes the administration of a therapeutically effective quantity of a therapeutic composition comprising fish roe and a member selected from the group consisting of Ginkgo biloba, Ginko biloba leaf extract, yohimbine, yohimbine hydrochloride, clomiphene and clomiphene citrate to male humans and animals. This method also includes the administration of a therapeutically effective quantity of a therapeutic composition comprising fish roe alone and in a formulation with a member selected from the group consisting of Ginkgo biloba, Ginkgo biloba leaf extract, estrogens, clomiphene and clomiphene citrate.

DETAILED DESCRIPTION OF THE INVENTION

Fish roe is commercially known as caviar and is prepared by removing the egg masses from freshly caught fish. Most caviar is processed in Russia and Iran from fish taken from the Caspian or Black Seas. Caviar from the Sturgeon species is among the highest quality commercially available and it has played an important role in the diets of people around the world for centuries. When fish roe, particularly sturgeon roe, was dried and lyophilized, by methods known in the art, and administered to humans and animals it was found to have a pronounced effect in treating sexual dysfunction and improving fertility.

In a first embodiment, the present invention relates to a composition for treating sexual dysfunction and infertility and improving sexual desire in humans and animals comprising fish roe, preferably sturgeon roe, even more preferrably dried, lyophilized sturgeon roe, administered orally to both humans and animals or via gastric tube to animals.

In a further embodiment, the invention relates to a method for the treatment of sexual dysfunction and the improvement of sexual desire in humans and animals and involves the administration of a therapeutic dose of fish roe, preferably sturgeon roe, even more preferrably dried, lyophilized sturgeon roe, orally to humans and animals or via gastric tube to animals. It has been found that the combination of roe and a member selected from the group consisting of Ginkgo biloba and Ginkgo biloba leaf extract produces a synergistic action in treating sexual dysfunction and improving sexual desire in humans and animals. This combination can be administered orally to humans and animals or via gastric tube to animals.

A further embodiment of the invention relates to treating erectile dysfunction and improving penile erection in male humans and animals and involves the administration of a therapeutic dose of fish roe, preferably sturgeon roe, even more preferrably dried, lyophilized sturgeon roe, orally to humans and animals or via gastric tube to animals. The effect on penile erection in male humans and animals is enhanced by the addition of a member selected from the group consisting of Ginkgo biloba, Gibkgo biloba leaf extract, yohmbine, and yohimbine hydrochloride. This combination can be administered orally to humans and animals or via gastric tube to animals.

Another embodiment of the invention relates to treating sexual dysfunction and improving sexual desire and vaginal lubrication, sensitivity, and engorgement in female humans and animals and involves the administration of a therapeutic dose of fish roe, preferably sturgeon roe, even more preferrably dried, lyophilized sturgeon roe, orally to humans and animals or via gastric tube to animals. It has been found that the increased sexual desire and increased vaginal lubrication, sensitivity, and engorgement in female humans and animals is further increased by the addition of a member selected from the group consisting of Ginkgo biloba, Ginkgo biloba leaf extract and estrogens. This combination can be administered orally to humans and animals or via gastric tube to animals.

Yet another embodiment of the invention relates to treating infertility in humans and animals and involves the administration of a therapeutic dose of fish roe, preferably sturgeon roe, even more preferrably dried, lyophilized sturgeon roe, orally to humans and animals or via gastric tube to animals. It has been found that there is a synergistic action in the treatment of infertility in humans and animals by the combination of fish roe with a member selected from the group consisting of Ginkgo biloba, Ginkgo biloba leaf extract, clomiphene and clomiphene citrate. This combination can be administered orally to humans and animals or via gastric tube to animals.

Obviously, various omissions, modifications, substitutions, and changes in the forms and details of the formulations illustrated and in their operation can be made by those skilled in the art without departing in any way from the spirit and scope of the present invention. Accordingly, it will be appreciated by those skilled in the art that within the scope of the appended claims, the invention may be practiced other than has been specifically described herein.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims:

1. A method for the treatment of erectile dysfunction and the improvement of penile erection in male humans and animals comprising the step of administering a therapeutically effective quantity of a therapeutic composition comprising sturgeon fish roe and a member selected from the group consisting of Ginkgo biloba, Ginkgo biloba leaf extract, yohimbine, and yohimbine hydrochloride to a human and an animal in need thereof.

2. The method for the treatment of erectile dysfunction and the improvement of penile erection in male humans and animals according to claim 1, wherein said sturgeon roe is dried, lyophilized sturgeon roe.

3. The method for the treatment of erectile dysfunction and the improvement of penile erection in male humans and animals according to claim 1, wherein said therapeutic composition is administered orally to humans and animals.

4. The method for the treatment of erectile dysfunction and the improvement of penile erection in male humans and animals according to claim 1, wherein said therapeutic composition is administered via gastric tube to animals.

5. The method for the treatment of erectile dysfunction and the improvement of penile erection in male humans and animals according to claim 2, wherein said therapeutic composition is administered orally to humans and animals.

6. The method for the treatment of erectile dysfunction and the improvement of penile erection in male humans and animals according to claim 2, wherein said therapeutic composition is administered via gastric tube to animals.

* * * * *